United States Patent [19]

Knifton et al.

[11] Patent Number: 5,276,215
[45] Date of Patent: Jan. 4, 1994

[54] ALKYLPHENOL SYNTHESIS USING ZEOLITES AS CATALYSTS, PARTICULARLY DEALUMINIZED Y-ZEOLITES

[75] Inventors: John F. Knifton, Austin, Tex.; Yu-Hwa E. Sheu, Hsinchu, Taiwan; Pei-Shing Dai, Port Arthur, Tex.

[73] Assignee: Texaco Chemical Company, White Plains, N.Y.

[21] Appl. No.: 44,424

[22] Filed: Apr. 9, 1993

[51] Int. Cl.⁵ .................................... C07C 37/14
[52] U.S. Cl. ........................ 568/794; 423/DIG. 21; 568/784; 568/791
[58] Field of Search ............... 568/791, 794, 786, 789; 423/DIG.

[56] References Cited

U.S. PATENT DOCUMENTS

| | | | |
|---|---|---|---|
| 3,130,007 | 4/1964 | Breck | 423/DIG. 21 |
| 4,275,249 | 6/1981 | Firth | 568/789 |
| 4,283,573 | 8/1981 | Young | 568/794 |
| 4,371,714 | 2/1983 | Young | 568/628 |
| 4,418,223 | 11/1983 | Firth | 568/794 |
| 4,532,368 | 7/1985 | Swanson et al. | 568/791 |
| 4,927,979 | 5/1990 | Yamagishi et al. | 568/791 |
| 4,954,663 | 9/1990 | Marler et al. | 568/791 |
| 5,015,785 | 5/1991 | Steck et al. | 568 X/783 |
| 5,072,054 | 12/1991 | Marler et al. | 568/794 |

*Primary Examiner*—Werren B. Lone
*Attorney, Agent, or Firm*—Kenneth R. Priem; James L. Bailey; Cynthia L. Kendrick

[57] ABSTRACT

Disclosed is a one-step method for synthesis of alkylphenols which comprises reacting phenol with the corresponding olefin under adiabatic conditions in the presence of a zeolite catalyst, preferably a dealuminated Y-zeolite, a modified Y-zeolite, or a β-zeolite.

24 Claims, No Drawings

ALKYLPHENOL SYNTHESIS USING ZEOLITES AS CATALYSTS, PARTICULARLY DEALUMINIZED Y-ZEOLITES

BACKGROUND OF THE INVENTION

1. Field of the Invention

The invention relates to a one step method for the preparation of alkylphenols from phenol and the corresponding olefin. More particularly it relates to a one-step method for preparation of alkylphenols by reacting phenols and the corresponding olefins over a zeolite molecular sieve catalyst. A particularly effective catalyst is dealuminized Y-zeolite. The method is especially effective in the synthesis of the most desirable para-alkyl phenol, for example, para-nonylphenol, from phenol and nonene.

2. Description of the Related Art

It is known in the art to prepare higher molecular weight alkylphenols, such as p-tert-octylphenol, p-nonylphenol and dodecylphenol by alkylating phenol with diisobutylene, propylene trimer and propylene tetramer, respectively, under acidic conditions. Nonylphenol, in particular, is used as an intermediate for surfactants, as well as antioxidants and lube oil additives.

In "Bisphenol A and Alkylated Phenols", SRI PEP Report No. 192 (December 1988), page 4-4, it is reported that it is known in the art to prepare various alkylphenols by acid catalyzed reactions of phenols with various olefins. These alkylphenols may include p-tert-butylphenol, p-isopropylphenol, p-sec-butylphenol, p-tert-octylphenol, nonylphenol and dodecylphenol. The alkylation reaction takes place at or near atmospheric pressure in the presence of an acidic catalyst such as a mineral acid, a Lewis acid (e.g. boron trifluoride) or a cation exchange resin (e.g. styrene-divinyl benzene resin). The acid catalysts lead to predominantly para-alkylated phenol when the para position is available. Generally a molar ratio of phenol to olefin of 1.5-3:1 is desired to minimize the yield of dialkylphenols.

U.S. Pat. No. 4,198,531, to BASF, discloses a process for continuous manufacture of p-alkylphenols by reacting phenol with olefin at 70°-140° C. in a fixed bed of an organic sulfonic acid cation exchange resin.

A Lewis acid or Bronsted acid catalyst is employed in U.S. Pat. No. 4,096,209 to Ciba-Geigy to prepare a phosphorylated butylated phenol/phenol ester mixture.

In U.S. Pat. No. 2,684,389 to Gulf R & D a phenol and mono-olefin are mixed in the presence of a silica-alumina adsorbent catalyst at 137° C. A silica-alumina catalyst is also employed in U.S. Pat. No. 3,876,710 to Hitachi to produce PTBP from phenol and isobutylene.

A $BF_3$ catalyst is used for the reaction of phenol and isobutene in British Patent 1,294,781 to Hoechst where the product cooled to form crystals which are crushed before ammonia is added to remove the catalyst. British Patent 1,249,571 is related.

In German Offen. 3,443,736 to Huels the catalyst is a sulfonated polystyrene ion exchange catalyst. U.S. Pat. No. 4,461,916, also to Huels, discloses a two-stage approach for producing p-tert-octylphenol using an acid ion exchange resin. U.S. Pat. No. 4,236,033 and U.S. Pat. No. 4,168,390 to Huels also disclose ion exchange resins, the latter comprising a LEWATIT ® resin deactivated with $Al_2(SO_4)_3$.

British Patent 2,120,953 to ICI discloses a process for producing nonylphenol by reacting diisobutene with phenol in the presence of a catalyst comprising fuller's earth with alkyl or aryl phosphate or phosphate ester.

U.S. Pat. No. 3,872,173 to Progil discloses the reaction of gaseous isobutene with liquid phenol in the presence of an acid-activated clay, again in two steps.

A highly acidic aryl sulfonic acid catalyst is employed in U.S. Pat. No. 3,932,537 to react phenol with isobutene under anhydrous conditions.

U.S. Pat. No. 3,422,157 to Union Carbide employs a cation exchange resin catalyst.

British Patent 131,4,623 to Union Rheinische Braunkohlen discloses an activated, acid-free, bleaching earth catalyst.

In U.S. Pat. No. 4,260,833, to UOP, phenol and isobutylene are reacted at 250° C. in the presence of a lithiated alumina catalyst. U.S. Pat. No. 3,929,912 discloses a more general alkylation of phenol and olefins in the presence of hydrogen fluoride and carbon dioxide.

An aluminum phenoxide catalyst is used for the orthoalkylation of phenol with butene-1 in French Patent 2,296,610, and U.S. Pat. No. 3,766,276, to Ethyl, as well as U.S. Pat. No. 3,933,927.

A boron trifluoride catalyst is used for the alkylation of phenol in U.S. Pat. No. 3,317,612.

Activated earth and phosphoric acid are used in a liquid phase transalkylation process in British Patent 1,444,935.

Acids are also useful for the condensation of phenol with acetone. Representative acids include an aromatic sulfonic acid (German Offen. 2,811,182 and U.S. Pat. No. 4,387,251), a volatile acid catalyst (U.S. Pat. No. 2,623,908), a strong mineral acid such as HCl or $H_2SO_4$ (U.S. Pat. No. 2,359,242), hydrochloric acid (U.S. Pat. No. 4,517,387), $H_2SO_4$ or HCl and 2-(4-pyridyl)ethanethiol (Japanese Kokai 57-118528), concentrated HCl (Japanese Kokai 60-38335) and hydrogen chloride (U.S. Pat. No. 4,169,211).

The SRI PEP Report, supra, does not suggest the use of a zeolite to facilitate this type reaction.

Zeolites—Background

Zeolites are widely found in natural deposits. More than 30 zeolites occur naturally. Early developments in zeolites were limited by the choices of naturally occurring types. A new class of industrial materials, molecular sieve zeolites were first introduced by Union Carbide in 1954. The discovery of methods for zeolite synthesis that used large organic cations as templates in the place of the traditional all-inorganic species, opened the way to the synthesis of many new zeolites.

Over the last two or three decades, more than 150 zeolite species have been synthesized, including synthesized zeolites such as A, X, Y and ZSM-5. This development is discussed further in an article titled "Molecular Shape Selective Catalysis," in New Horizons in Catalysis, Part A, p. 3 (1980). P. B. Weisz reviews some of the opportunities in industry for the use of molecular shape selective catalysis. For example, due to intracrystalline molecular shape selectivity it is possible to catalyze the dehydration of n-butanol without reacting isobutanol on a Linde 5A zeolite.

The characteristic structures of catalytically important molecular sieve zeolites are discussed in "Molecular Sieve Catalysts," by J. W. Ward, Applied Industrial Catalysis, Vol. 3, Ch. 9, p. 271 (1984).

The synthetic X and Y type zeolites have framework structures similar to that of the natural mineral faujasite although each is a distinct species. The unit cells are cubic with a cell dimension of nearly 25Å. Each unit cell contains 192 $SiO_4$ and $AlO_4$ tetrahedra that are linked through shared oxygen atoms. The three-dimensional framework gives rise to giant supercages approximately 13Å in diameter. There are eight supercages per unit cell. The supercages are interconnected by twelve-membered rings of about 8Å in diameter. The large-pore system is three-dimensional and absorption measurements show that many different chemical species are absorbed. The cation sites that exist inside the supercage or close to the walls of the supercages are probably most important.

One type of faujasite is mordenite. It has a $SiO_2/Al_2O_3$ ratio of about 10. The structure consists of chains of tetrahedra cross-linked by sharing of oxygen atoms. A large number of five-membered rings that are energetically favored probably explain the high thermal stability. In contrast, the dehydrated structure has a two dimensional channel system accessible to small molecules but not to typical hydrocarbons.

Erionite is probably the smallest pore zeolite used commercially. It is one of the most siliceous naturally occurring zeolites, having a silica/alumina ratio of about 6.

Aluminum-rich zeolites such as A and X have Si/Al ratios from 1 to 1.5. "Industrial Catalytic Applications of Molecular Sieves" by P. R. Pujadó, et al. in Catalysis Today, 13, 113 (1992). Many of the synthesized zeolites and molecular sieves have a $SiO_2/Al_2O_3$ ratio of greater than 10, Ward, supra, p. 9. Silicon-rich zeolites typically have a Si/Al ratio of from about ~10 to 100, see Pujadó, et al., supra, p. 115 The aluminum-free, silicalite, has essentially no ion-exchange properties and, therefore, should be regarded as a molecular sieve, see Ward, supra, p. 9. Certain of a new family of aluminum phosphate molecular sieves are analogs of aluminosilicate zeolites. $AlPO_{4-17}$ is structurally analogous to erionite and $AlPO_{4-20}$ has a structure similar to sodalite. These are molecular sieves, Ward, supra, pp. 277, 280.

Generally, it can be said that changes in the Si/Al ratio from 1 to infinity result in predictable changes in:
Stability, from <700° C. to ~1300° C.
Surface selectivity, from hydrophilic to hydrophobic
Acidity increasing in intrinsic strength
Cation concentration decreasing
Structure from 4-, 6- and 8-rings to 5-rings.

The thermal stability of the crystalline lattice of zeolites also varies substantially, from about 700° C. for aluminum-rich zeolites, to about 1300° C. for silicalite. Aluminum-rich zeolites are unstable in the presence of acids, while silicon-rich zeolites are stable even in concentrated mineral acids. In contrast, silicon-rich zeolites exhibit low stability in basic solutions. Likewise, aluminum-rich zeolites exhibit a highly-polar hydrophilic surface. Silicon-rich zeolites tend to be more nonpolar and hydrophobic. The onset of hydrophobicity appears to occur at a Si/Al ratio of about 10.

Though molecular sieve zeolites with aluminum or silicon as the tetrahedral cations generally have higher thermal and hydrothermal stability, high acidity and lower cost of synthesis, the zeolite framework can be substituted by other closely related elements in the periodic table. Pujadó, et al., supra, p. 120.

Borosilicate catalysts prepared by the substitution of B for Al in ZSM-5 have been disclosed as practical catalysts for shape-selective acid catalysis. For example, the gallium-framework substituted form of ZSM-5 is known to catalyze the aromatization of propane and butane.

Another class of useful, strongly acidic zeolites are derived from β-zeolites. For a description of the structure and uses of β-zeolites see J. B. Higgins et al., Zeolites, 1988, Vol. 8, p. 446, T. C. Tsai and I. Wang, Applied Catalysis, 77, p. 199 and 209 (1991) and P. A. Parikh et al., Applied Catalysis A, 90, 1 (1992).

Aluminophosphate molecular sieves, first reported in 1982 include very large pore material, VPI-5, which has a unidimensional channel of an 18-membered ring with a free pore diameter of 1.25 mn. These zeolites are neutral frameworks, having no ion-exchange capacity. Some members of the series (although not the large pore material) exhibit excellent thermal and hydrothermal stability, up to 1000° C. and 600° C., respectively.

Other new families of molecular sieves include silicoaluminophosphates, metal aluminophosphates and metal silicoaluminophosphates. Ibid, p. 135, it is stated that medium-pore aluminophosphate-based molecular sieves are active and selective catalysts for a variety of important hydrocarbon conversion reactions. As acid catalysts, they promote olefin isomerization and oligomerization, but they are less effective at the competing hydride transfer and cracking reactions. Applications which look promising include catalytic dewaxing, p-xylene production, olefin isomerization, conversion of methanol to light olefins, alkylation of aromatics with methanol and octane-enhancing catalyst additives.

Most industrial reactions conducted over molecular sieves are acid catalyzed reactions, Ward, supra, p. 286. It is often necessary to modify the zeolites to introduce the acidic catalytic sites or to improve thermal and chemical stability. This is accomplished by:
1) cation exchange
2) thermal and hydrothermal treatment
3) chemical modification.

Where ammonium exchange is employed in order to obtain high levels of exchange, elevated temperatures and excess ammonium salt should be used. For example, the zeolite may be refluxed with at least five-fold excess of an aqueous ammonium salt for several hours. Exchange may be increased by repeated batchwise treatments, however it is extremely difficult to obtain 100% exchange of sodium.

Divalent cations, such as calcium and magnesium may be exchanged into X and Y zeolites only with some difficulty. In order to exchange trivalent ions, multiple batch exchanges at elevated temperatures with excess solutions are required.

Though direct hydrogen ion exchange occurs readily in zeolites to a limited extent on water washing, it can be difficult to achieve higher degrees of exchange because zeolites are acid sensitive, however the stability to acids increase with Si/Al ratio. Therefore, Y-zeolite can withstand a lower pH of about 3, whereas X zeolite is destroyed at a pH of about 4. Careful acid treatment can result in u to 75% of the alkali metal ions being replaced before structural collapse occurs.

It is possible to employ various combinations of calcination and ion exchange in preparing a catalyst. For example, one can exchange with ammonium ions, calcine and exchange with rare-earth ions. Another consequence of thermal treatment of multivalent cation zeolites is the generation of acidity.

On heating zeolites the first observation is loss of physically bound water, resulting in an endotherm near 150° C. At about 400° to 500° C. the zeolite is substantially dehydrated. The observation of endotherms and exotherms seems to be affected by whether the atmosphere is air or inert. Thermal treatment of synthesized X and Y zeolites has no significant structural effects on the zeolite until the decomposition temperature of at least about 800° C. is reached.

One of the last absorption bands to disappear with heating is hydroxyl groups. Some of the hydroxyl groups are believed to be located in the supercages and some are believed to possibly be in the hexagonal prism portions of the structure and inaccessible to most absorbing molecules.

Of the methods available for modifying the zeolite structure other than acid treatment, chelation by acetylacetone and ethylenediamine tetracetic acid and treatment with fluorine strictly remove alumina from the structure while treatment with silicon tetrachloride and ammonium fluorosilicate replaces aluminum atoms with silicon.

For many industrial reactions, the addition of metals, their oxides, or sulfides, are necessary to perform the total or partial catalytic function Many metal ions can be introduced by ion exchange. Metals such as nickel, cobalt, silver, chromium and iron can be directly exchanged from aqueous solutions of their salts such as nitrates, chlorides, acetates and the like. Metals can also be introduced by impregnation, wherein the metal compounds are dissolved in a suitable solvent, commonly water, aqueous ammonia, dilute phosphoric acid, etc.

Zeolites, particularly aluminosilicate zeolites have found many uses as catalysts in the petrochemical industry. In fluidized catalytic cracking the use of rare-earth exchanged Y-zeolites evolved to steam-stabilized Y, and then to aluminum depleted Y, and finally to silicon-enriched Y.

In hydrocracking all zeolite-based catalysts contain Y-zeolite. The large pore size, three-dimensional pore lattice and corresponding high diffusivity, high acidity and molecular sieve action of the Y-zeolite provide an excellent combination of desirable characteristics for a catalyst in the cracking of large molecules, such as those found in vacuum gas oil.

Mordenite or ZSM-5 alone or in combination with transition metals have been reported in commercial use for catalytic dewaxing applications.

In the isomerization of paraffins, conventional halide non-zeolite catalysts are used predominantly, however mordenite-based zeolite catalysts have a substantial market share based on their enhanced tolerance of feed impurities.

Other reactions which typically use some form of zeolite include aromatic alkylation reactions, disproportionation and transalkylation of aromatics and isomerization of xylenes. However Pujadó, et al. make no reference to the synthesis of alkylphenols.

An excellent review of the uses of shape selective catalysis in industry is found in an article titled "Zeolite Advances in the Chemical and Fuel Industries: A Technical Perspective," by T. E. Whyte et al., Catal. Rev.-Sci. Eng. 24(4), pp. 567–598 (1982).

According to Whyte et al., the first milestone in zeolite catalysis was the observation that small quantities of zeolites incorporated in silica, silica-alumina and silica-clay materials significantly improved the properties. Next was the observation that high conversion rates could be obtained through the intracrystalline pore channel system, which was termed "shape selectivity."

The third milestone was Barren's crystallization of synthetic counterparts of certain zeolite minerals.

Shape selectivity can be divided into three classical types. The first type occurs when only a fraction of reactant molecules are able to penetrate the intracrystalline pores. The second, product shape selectivity, is observed when one or more of the products formed from the substrate molecules has a slower rate of diffusion relative to other products. Finally, restricted transition state selectivity occurs in zeolite systems when the transition state complex required for a given reaction pathway cannot form in the catalyst pores because it is larger than the zeolite pore itself.

Shape selectivity includes selectoforming, M-forming and dewaxing. Toluene disproportionation, xylene isomerization and MTG technologies are based on either restricted transition state, product shape-selective principles or a combination thereof. It has become apparent that there are a number of possibilities with zeolites and that the interface between homogeneous and heterogeneous catalysis may be closing where the zeolite structure is used as a "solvent", or anchor, for homogeneous catalysts, metal clusters and alloys.

Focusing again on the known processes for producing alkylphenols, generally the processes require two stages for achieving thermodynamic equilibrium and many of the catalysts are not stable at high temperatures. In addition, it is often difficult to obtain a high para- to ortho- ratio or to obtain, in the case of nonylphenol synthesis, more mononylphenol relative to dinonylphenol; and, from the art, it would appear that conversions of about 80% are about the most which could be expected in any process to prepare alkylphenols.

It would be a distinct advance in the art if alkylphenols such as nonylphenols and particularly para-nonylphenols could be prepared in one step with a high conversion of nonene. It would be particularly desirable if the catalyst exhibited high thermal stability. Such a process would be especially attractive commercially if the system were operated adiabatically, since close temperature control, cooling and recycling make many processes considerably more expensive to build and operate.

It is an object of the instant invention to provide a one-step process for the synthesis of alkylphenols in high yield and with almost complete conversion of olefin using a catalyst system which can operate under adiabatic conditions and exhibits stability even at elevated temperatures. Another object is to obtain high selectivity to desired alkylphenol while, at the same time, producing a high ratio of para- to ortho- alkylphenol.

SUMMARY OF THE INVENTION

In accordance with the foregoing the novel method of the instant invention for preparing alkylphenols comprises reacting a phenol with the corresponding olefin in the presence of a catalyst comprising a zeolite, particularly a dealuminized Y-zeolite, at a temperature from about 60° C. to 250° C.

DESCRIPTION OF THE PREFERRED EMBODIMENT

Preparation of the product of this invention may be carried out typically by reacting the phenol and the olefin under adiabatic conditions. The products demonstrate high selectivities and yields. In the examples where the olefin is nonene, the product is made up of a large ratio of the most desirable form of nonylphenol, para-nonylphenol, compared to ortho-nonylphenol.

The reaction can be represented by the following:

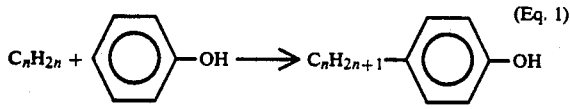

where n is three or greater, preferably in the range 4 to 12.

The olefins which are useful in the instant invention are those which are often available from petrochemical operations. Examples include propylene, 1- and 2-butenes, isobutene and isopentene. Others include isoheptene, diisobutylene, mixed octenes, mixed nonenes, decenes and dodecenes or carbon mixtures thereof. In addition higher straight chain olefins produced by ethylene oligomerization or by dehydrogenation or chlorination-dehydrochlorination of straight chain paraffins are also useful.

Preferred olefins are $C_6$-$C_{12}$ olefins and particularly useful are mixed octenes and mixed nonenes, or mixtures thereof. The examples herein demonstrate the production of p-nonylphenol, which is the preferred form of an important specialty chemical. Nonylphenol is in demand as an intermediate for surfactants, antioxidants and lubricating oil additives.

The catalysts suitable for the practice of this invention generally comprise dealuminated Y-zeolite catalysts, $\beta$-zeolites and triflic acid-treated Y-zeolites. Methods of dealuminating the Y-zeolites which have been found effective include:

1. Dealumination produced by:
   a) Ammonium exchange, followed by calcination;
   b) Chelation of alumina by treatment with EDTA;
   c) Treatment of the zeolite with fluorine, hydrofluoric acid, or a fluorine-containing reactant; and
   d) Hydrothermal and/or acid treatment reagents.

The preferred catalysts for use in the dealuminated form for the reaction of Eq. 1 are certain crystalline aluminosilicate zeolites, particularly the isostructural group of faujasite zeolites that include the synthetic X- and Y-zeolites. The preferred zeolites for dealumination are the Y-zeolites.

The unit cells of faujasite zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Dealumination changes this ratio. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or $\beta$-cage, can be represented by a truncated octahedron, with the 24 silicon or aluminum atoms(designated T atoms) taking positions at the vertices. The 36 oxygen atoms are displaced from the midpoints of the edges joining the vertices in order to attain tetrahedral configuration around the T atoms. The free diameter of the void within the $\beta$-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed $\alpha$-cages, or supercages. The $\alpha$-cage is a 26-hedron with a free diameter of $\approx 1.3$ nm, and it can be entered through four distorted 12-member rings of diameter 0.80–0.90 nm. In this way each $\alpha$-cage is tetrahedrally joined to four others giving a complex system of void space extending throughout the zeolite structure. The $\alpha$- and $\beta$-cages together give Y-zeolites, along with X-zeolites, the largest void volume of any known zeolites, which is ca. 50 vol % of the dehydrated crystal. From the catalytic viewpoint, the $\alpha$-cages are by far the most important, since, unlike the $\beta$-cages, they permit entry of numerous aliphatic and aromatic compounds.

It has been demonstrated in the instant invention the Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents, or by treatment with fluorine or a fluorine-containing agent such as hydrogen fluoride, ammonium fluorosilicate, or lanthanide-containing agents. Said dealuminated Y-zeolites should have a silica-to-alumina molar ratio of greater than three, preferably a ratio of 5 or greater and most preferably a silica-to-alumina ratio of 5 to 100.

A further possibility is that said Y-zeolite may be treated with steam, or acid, or a combination of steam followed by acid.

The catalysts used in the examples included are a Y-zeolite having a $SiO_2/Al_2O_3$ molar ratio of 46, surface area of 775 m$^2$/g and unit cell size of 24.26Å as 1/16" extrudates. Another comprised a rare earth exchanged Y-zeolite having a Si/Al ratio of 1.5→2 having 10–20% alumina binder (SK-500 in 1/16" extrudates). One catalyst comprises an ultrastable Y-zeolite having a silica/alumina molar ratio of 6.5, a surface area of 800 m$^2$/g and a unit cell size of 24.56Å.

Other catalysts included an ammonium-exchanged Y-zeolite having a silica/alumina ratio of 7.8 and a unit cell size of 24.53Å and an ultrastable Y-zeolite, in sodium form having a silica/alumina molar ratio of 5.3, a surface area of 750 m$^2$/g and a unit cell size of 24.51Å. Still other examples include a triflic acid-modified SK-500, a hydrogen fluoride-modified SK-500 and a sample of $\beta$-zeolite.

The molar ratio of the olefin to phenol can vary, but is generally in the ratio of 1:5–5:1. The preferred molar ratio is about 1:1.

Preparation of alkylphenols is conducted in a fixed bed, continuous flow reactor.

The reaction is conducted under adiabatic conditions. The "hot spot" or maximum temperature of the reactor can be in the range of 60°-250° C. and preferably 80° C. to 140° C. The preferred temperature depends on the choice of reactants, however, in the case of nonene and phenol an effective temperature is about 90° C. The pressure can be in the range of atmospheric to 1000 psi and is preferably about 100 psi.

Typically the alkylphenol is generated continuously in up to ca. 50 wt % concentration in the crude product liquid effluent.

Olefin conversions are high. Nonenes conversion is 50-80%. Preferably the nonenes conversion is >50% and the para-nonylphenol to ortho-nonylphenol weight ratio is >10.

These yields are achieved at a total liquid hourly space velocity (LHSV) of one to 10 under mild conditions.

Here LHSV is defined as follows:

$$LHSV = \frac{\text{Weight of Total Liquid Feed Run Through the Reactor Per Hour}}{\text{Volume of Catalyst in Reactor}}$$

Conversion of olefins (wt %) is estimated in the following examples using the equation:

$$100 - \left(\frac{\text{Wt \% Conc. of Olefin in Product}}{\text{Wt \% Conc. of Olefin in Feed}}\right) \times 100$$

Yields of alkylphenol (mole %) are estimated from:

$$\frac{\text{Moles of Alkylphenol in Product Liquid}}{\text{Moles of Olefin in Feed}} \times 100$$

The accompanying examples illustrate:

1. In Example i, using an ultrastable, dealuminized Y-zeolite catalyst, with a silica/alumina ratio of 46, run adiabatically, it is possible to achieve:
   a) 72% nonenes conversion per pass at 120° C., LHSV 1;
   b) A p-nonylphenol to o-nonylphenol ratio of 9.4 at the same set point temperature;
   c) A nonylphenol to dinonylphenol ratio of 7.6;
   d) 40% nonenes conversion per pass at a control temperature of 100° C., LHSV 3, where the hot spot temperature is at least 120° C.

2) In Examples 2-6, other Y-zeolites, in acidic and sodium forms, as well as mordenites show varying activities for the desired synthesis of paranonylphenol. The calculated conversions, nonylphenol total concentrations, para-to-ortho nonylphenol ratios as well as the nonylphenol to dinonylphenol ratios, are summarized in Table 8.

Particularly,
a) For SK-500, at a set point temperature of 120° C., the nonenes conversion is 53%.
b) For the ammonium-exchanged Y-zeolite, LZY-82, the nonylphenol to dinonylphenol product ratio is 86 at a set point operating temperature of 80° C.
c) For a Y-zeolite in sodium form, e.g. CP308-51, the para-nonylphenol to orthononylphenol ratio is 17.4 at 80° C.

In Examples 9-11, nonylphenol, particularly para-nonylphenol syntheses from phenol/nonene, are illustrated using:
a) A triflic acid-modified Linde SK-500 catalyst, prepared by the method of Example 7.
b) A hydrofluoric acid-modified Linde SK-500 catalyst, prepared by the method of Example 8.
c) A sample of β-zeolite (C861β from PQ Corp).

EXAMPLE 1

This example illustrates the selective production of para-nonylphenol from phenol and mixed nonenes using a dealuminized Y-zeolite catalyst.

Synthesis was conducted in a 500 cc capacity, tubular reactor constructed of stainless steel, operated upflow and fitted with temperature, pressure and flow rate regulating devices. The reactor was charged at the beginning of the experiment with 400 cc of dealuminized ultrastable Y-zeolite (CP 316-26 from PQ Corp., having a $SiO_2/Al_2O_3$ molar ratio of 46, surface area 775 m²/g, unit cell size 24.26Å, as 1/16" extrudates). A screen of glass wool was placed at the top and bottom of the reactor to ensure the catalyst would remain in the middle portion.

Said catalyst bed was treated with a phenol/nonene mix (1:1 weight ratio, 1.34:1 molar ratio) upflow, at a rate of 400 cc/hr, while the first section of the catalyst bed was held at 80° C. The reactor was run adiabatically and the hot spot temperature along the catalyst bed was at least 87° C.; total pressure was 100 psi. Samples of crude product effluent were collected after the unit had reached steady state conditions and analyzed by glc and gpc. Typical analyses data are given in Table 1.

The experiment was repeated at a series of temperatures (100°, 120° C.) and flow rates 1800, 1200 cc/hr) under adiabatic conditions. These runs and results data are also given in Table 1. Typical calculated nonene conversion levels and nonylphenol/dinonylphenol, plus para/ortho-nonylphenol product weight ratios are given in Table 2.

TABLE 1

| | | | | | | NONYLPHENOL PRODUCT COMPOSITION | | | | | | | |
|---|---|---|---|---|---|---|---|---|---|---|---|---|---|
| | | | | | | | glc | | | lc | | | Hot Spot |
| Ex. | Catalyst | PhOH/C₄H₈ Molar Ratio | Control Temp. (°C.) | Feed Rate (cc/hr) | Sample | Temp (°C.) | C₉H₁₈ | PhOH | NP | DNP | NP/DNP | o-NP | p-NP |
| 1 | CP316-26 | 1.34 | | | FS-1 | 50.7 | 49.2 | | | | | | |
| | | | 80 | 400 | 1 | 19.4 | 30.9 | 42.4 | 7.1 | 10.6 | 7.2 | 57.5 | 87 |
| | | | 100 | 400 | 2 | 16.3 | 29.2 | 47.3 | 7.1 | 12.6 | 6.3 | 64.5 | 114 |
| | | | 120 | 400 | 3 | 14.0 | 27.9 | 49.5 | 8.1 | 13.1 | 8.1 | 75.9 | 131 |
| | | | 100 | 800 | 4 | 25.2 | 34.4 | 35.2 | 5.0 | 12.0 | 8.4 | 76.4 | 119 |
| | | | 100 | 1200 | 5 | 30.5 | 36.8 | 29.0 | 3.7 | 11.2 | 9.1 | 75.9 | 120 |

TABLE 2

NONYLPHENOL PRODUCT ANALYSES DATA

| Ex. | Sample | Control Temp. (°C.) | LHSV | Nonene Conv (%) | NP Conc (%) | Weight Ratio p-NP/o-NP | NP/DNP |
|---|---|---|---|---|---|---|---|
| 1 | 1 | 80 | 1 | 62 | 42 | 8.0 | 6.1 |
|   | 3 | 120 | 1 | 72 | 50 | 9.4 | 6.4 |
|   | 5 | 100 | 3 | 40 | 29 | 8.3 | 7.6 |

EXAMPLES 2-6

These examples illustrate the selective production of para-nonylphenol from phenol and mixed nonenes using a variety of other Y-zeolite catalysts.

Following the procedures of Example 1, a series of Y-zeolites were treated with phenol/nonene feed mix (1.34:1 molar ratio) under adiabatic operating conditions, at a series of temperatures (80°-120° C.) and feed rates (400-1200 cc/hr). The catalysts tested comprised:

a) A rare-earth exchanged Y-zeolite with a silica/alumina ratio of 1.5→2, having 10-20% alumina binder (SK-500, 1/16" extrudates, from UOP Corp.). Results are given in Table 3.

b) An ultrastable Y-zeolite, having a silica/alumina molar ratio of 6.5, a surface area of 800 m²g and a unit cell size of 24.56Å (CP316-56, 1/16 extrudates, from PQ Corp.). Results are summarized in Table 4.

c) An ammonium-exchanged Y-zeolite having a silica/alumina ratio of 7.8 and a unit cell size of 24.53Å (LZ-482, 1/16" extrudates, from UOP Corp.). Results are summarized in Table 5.

d) An ultrastable Y-zeolite, in sodium form, having a silica/alumina molar ratio of 5.3, a surface area of 750 m²/g and a unit cell size of 24.51Å (CP308-51, 1/8" extrudates, from PQ Corp.). Results are summarized in Table 6.

Calculated nonene conversion levels, as well as nonylphenol/dinonylphenol and para/ortho-nonylphenol product weight ratios, are given in Table 8 for selected experiments.

TABLE 3

NONYLPHENOL PRODUCT COMPOSITION

| Ex. | Catalyst | PhOH/C$_4$H$_8$ Molar Ratio | Control Temp. (°C.) | Feed Rate (cc/hr) | Sample | glc C$_9$H$_{18}$ | PhOH | NP | DNP | lc DNP | o-NP | p-NP |
|---|---|---|---|---|---|---|---|---|---|---|---|---|
| 2 | SK-500 | 1.34 |  |  | FS-1 | 50.9 | 48.7 |  |  |  |  |  |
|   |   |   | 80 | 400 | 1 | 32.3 | 38.9 | 25.8 | 3.0 | 11.5 | 6.7 | 77.4 |
|   |   |   | 100 | 400 | 2 | 24.7 | 35.0 | 35.5 | 4.7 | 11.6 | 6.1 | 78.7 |
|   |   |   | 120 | 400 | 3 | 23.7 | 32.0 | 39.1 | 5.2 | 11.9 | 7.6 | 76.9 |
|   |   |   | 100 | 800 | 4 | 32.3 | 38.7 | 26.4 | 2.6 | 9.30 | 7.1 | 78.8 |
|   |   |   | 100 | 1200 | 5 | 35.3 | 39.8 | 22.8 | 2.1 | 8.92 | 7.4 | 78.3 |

TABLE 4

NONYLPHENOL PRODUCT COMPOSITION

| Ex. | Catalyst | PhOH/C$_4$H$_8$ Molar Ratio | Control Temp. (°C.) | Feed Rate (cc/hr) | Sample | glc C$_9$H$_{18}$ | PhOH | NP | DNP | lc DNP | o-NP | p-NP | Hot Spot (°C.) |
|---|---|---|---|---|---|---|---|---|---|---|---|---|---|
| 3 | CP316-56 | 1.34 |  |  | FS-1 | 51.1 | 48.9 |  |  |  |  |  |  |
|   |   |   | 80 | 400 | 1$^a$ | 77.9 | 21.8 | 0.3 | — | — | — | — | 82 |
|   |   |   |   |   |  | 28.1 | 71.5 | 0.4 |   |   |   |   |   |
|   |   |   | 100 | 400 | 2$^a$ | 70.3 | 28.8 | 0.9 | — | — | 4.8 | 19.3 | 100 |
|   |   |   |   |   |  | 48.9 | 50.4 | 0.7 |   |   |   |   |   |
|   |   |   | 120 | 400 | 3 | 48.2 | 49.9 | 1.9 | — | — | 4.9 | 57.0 | 129 |
|   |   |   | 100 | 400 | 4 | 50.4 | 48.9 | 0.7 | — | 2.0 | 5.2 | 36.8 | 140 |
|   |   |   | 100 | 100 | 5 | 49.9 | 48.5 | 1.5 | — | 1.7 | 5.8 | 52.4 | 153 |
|   |   |   | 80 | 400 | 1B$^b$ | 50.3 | 49.1 | 0.6 | — | — | 3.3 | 17.9 | 97 |
|   |   |   | 100 | 400 | 2B$^b$ | 49.0 | 49.4 | 1.6 | — | — | 5.4 | 52.4 | 128 |
|   |   |   | 120 | 400 | 3B$^b$ | 48.2 | 48.5 | 3.2 | — | — | 9.2 | 71.8 | 154 |

$^a$Two phase product
$^b$Repeat run

TABLE 5

NONYLPHENOL PRODUCT COMPOSITION

| Ex. | Catalyst | PhOH/C$_4$H$_8$ Molar Ratio | Control Temp. (°C.) | Feed Rate (cc/hr) | Sample | glc Temp C$_9$H$_{18}$ | PhOH | NP | DNP | lc DNP | o-NP | p-NP | Hot Spot (°C.) |
|---|---|---|---|---|---|---|---|---|---|---|---|---|---|
| 4 | CP316-26 | 1.34 |  |  | FS-1 | 52.7 | 47.3 |  |  |  |  |  |  |
|   |   |   | 80 | 400 | 1 | 43.2 | 29.2 | 27.2 | 0.3 | 1.1 | 6.8 | 88.2 | 86 |
|   |   |   | 100 | 400 | 2 | 32.5 | 35.5 | 31.4 | 0.6 | 1.3 | 7.2 | 88.2 | 102 |
|   |   |   | 120 | 400 | 3 | 29.0 | 33.8 | 36.4 | 0.8 | 2.1 | 8.5 | 86.1 | 120 |
|   |   |   | 100 | 800 | 4 | 38.2 | 37.2 | 24.2 | 0.4 | 1.3 | 8.6 | 85.8 | 132 |

TABLE 5-continued

NONYLPHENOL

| Ex. | Catalyst | PhOH/C₄H₈ Molar Ratio | Control Temp. (°C.) | Feed Rate (cc/hr) | Sample | PRODUCT COMPOSITION glc C₉H₁₈ | PhOH | NP | lc DNP | DNP | o-NP | p-NP | Hot Spot (°C.) |
|---|---|---|---|---|---|---|---|---|---|---|---|---|---|
|  |  |  | 120 | 1200 | 5 | 32.1 | 35.8 | 31.3 | 0.7 | 2.4 | 13.0 | 77.0 | 186 |

TABLE 6

NONYLPHENOL

| Ex. | Catalyst | PhOH/C₄H₈ Molar Ratio | Control Temp. (°C.) | Feed Rate (cc/hr) | Sample | PRODUCT COMPOSITION glc C₉H₁₈ | PhOH | NP | lc DNP | DNP | o-NP | p-NP | Hot Spot (°C.) |
|---|---|---|---|---|---|---|---|---|---|---|---|---|---|
| 5 | CP316-51 | 1.34 |  |  | FS-1 | 46.0 | 53.9 |  |  |  |  |  |  |
|  |  |  | 80 | 400 | 1 | 40.3 | 41.2 | 18.4 | — | — | 5.2 | 90.4 | 81 |
|  |  |  | 100 | 400 | 2 | 28.9 | 33.2 | 37.6 | 0.3 | 0.7 | 5.1 | 91.7 | 100 |
|  |  |  | 120 | 400 | 3 | 22.0 | 28.3 | 49.0 | 0.8 | 1.3 | 5.9 | 90.5 | 120 |
|  |  |  | 100 | 800 | 4 | 35.5 | 40.2 | 24.1 | 0.1 | 0.7 | 5.3 | 90.4 | 100 |
|  |  |  | 100 | 1200 | 5 | 36.4 | 39.7 | 23.7 | 0.1 | 0.8 | 6.1 | 89.2 | 119 |

TABLE 7

NONYLPHENOL

| Ex. | Catalyst | PhOH/C₄H₈ Molar Ratio | Control Temp. (°C.) | Feed Rate (cc/hr) | Sample | PRODUCT COMPOSITION glc C₉H₁₈ | PhOH | NP | lc DNP | DNP | o-NP | p-NP | Hot Spot (°C.) |
|---|---|---|---|---|---|---|---|---|---|---|---|---|---|
| 6 | Zelon 900H | 1.34 |  |  | FS-1 | 52.7 | 47.3 |  |  |  |  |  |  |
|  |  |  | 80 | 400 | 1 | 51.5 | 47.7 | 0.8 | — | — | 5.4 | 23.5 | 87 |
|  |  |  | 100 | 400 | 2 | 51.5 | 46.9 | 1.6 | — | — | 7.2 | 51.1 | 120 |
|  |  |  | 120 | 400 | 3 | 51.1 | 46.1 | 2.4 | — | — | 8.7 | 66.5 | 135 |
|  |  |  | 100 | 800 | 4 | 52.0 | 47.1 | 0.9 | — | — | 8.1 | 29.1 | 143 |
|  |  |  | 100 | 1200 | 5 | 53.0 | 46.8 | 0.1 | — | — | 8.1 | 28.4 | 153 |

TABLE 8

NONYLPHENOL PRODUCT ANALYSES DATA

| Ex. | Catalyst | Control Temp. (°C.) | LHSV | Nonene Conv (%) | NP Conc (%) | Weight Ratio p-NP/o-NP | NP/DNP |
|---|---|---|---|---|---|---|---|
| 2 | SK-500 | 80 | 1 | 37 | 26 | 11.6 | 7.3 |
|  |  | 120 | 1 | 53 | 39 | 10.1 | 7.1 |
|  |  | 100 | 3 | 31 | 23 | 10.6 | 9.6 |
| 4 | LZ-Y82 | 80 | 1 | 18 | 27 | 13.0 | 86 |
|  |  | 120 | 1 | 44 | 36 | 10.1 | 45 |
|  |  | 100 | 3 | 39 | 31 | 5.9 | 38 |
| 5 | CP308-51 | 80 | 1 | 12 | 18 | 17.4 |  |
|  |  | 120 | 1 | 52 | 49 | 15.3 | 74 |
|  |  | 100 | 3 | 21 | 24 | 14.6 | 119 |

EXAMPLE 7

This example illustrates the synthesis of a triflic acid-modified Y-zeolite.

To 475 g of Linde SK-500, dried at 175° C. for 3 hours under vacuum (H₂O, 0.2%) was added a solution of triflic acid (trifluoromethanesulfonic acid, 200 g) in 2 liters of dried acetone. The mixture was stirred under nitrogen atmosphere overnight, filtered and the recovered solids washed with acetone and distilled water, then dried in vacuo (40° C., overnight, followed by 150° C., 4 hours).

The recovered, light-brown, extrudates (452 g) were found to comprise:
H₂O, 0.7%
Acidity, 0.84 meq/g

EXAMPLE 8

This example illustrates the synthesis of a hydrofluoric acid-modified Y-zeolite.

To 100 g of Linde SK-500 was added an aqueous solution of 48% hydrofluoric acid (50 g) in distilled water (100 g). The mixture was stirred overnight, filtered, and the recovered solids washed with distilled water and dried (40° C., overnight, followed by 150° C., 4 hours), under vacuum.

The recovered, white extrudates (80 g) were found to comprise:
F, 2.3%
H₂O, 0.63%
Acidity, 0.33 meq/g

EXAMPLES 9-11

These examples illustrate the selective production of para-nonylphenol from phenol and mixed nonenes using modified Y-zeolites and β-zeolite.

Following the procedures of Example 1, a series of acidic zeolites were treated with phenol/nonene feed mix 1:34 molar ratio) under adiabatic operating conditions, at a series of temperatures (80°-120° C.) and feed rates (400-1200 cc/hr). The catalysts tested comprised:
 a) A triflic acid-modified Linde SK-500 prepared by the method of Example 7. Results are given in Table 9.
 b) A hydrofluoric acid-modified Linde SK-500 prepared by the method of Example 8. Results are summarized in Table 10.
 c) A sample of β-zeolite, having a silica/alumina ratio of about 24, a surface area of ca. 600 m²/g, evaluated in 1/16" extruded form with 20% added alumina binder. Results are summarized in Table II.

temperature of from 60° C. to 250° C. and a pressure of near atmospheric to about 1000 psi.

2. The method of claim 1 wherein the olefin is selected from the group consisting of mixed octenes, mixed nonenes, mixed dodecenes and mixtures thereof.

3. The method of claim i wherein the olefin is mixed nonenes and the alkylphenols are nonylphenols.

4. The method of claim 1 wherein zeolite molecular sieve is a Y-zeolite.

5. The method of claim 1 wherein Y-zeolite is dealuminated in a manner selected from:
 a) ammonium exchanging the Y-zeolite followed by calcinating;
 b) treating the Y-zeolite with a fluorine-containing compound from the group consisting of hydrofluoric acid, silicon tetrafluoride and ammonium fluorosilicate.

6. The method of claim 5 wherein the dealuminized Y-zeolite has a silica-to-alumina molar ratio of 5 or greater.

TABLE 9
NONYLPHENOL

| Ex. | Catalyst | PhOH/C₄H₈ Molar Ratio | Control Temp. (°C.) | Feed Rate (cc/hr) | Sample | glc Temp C₉H₁₈ | PhOH | NP | lc DNP | DNP | o-NP | p-NP | Hot Spot (°C.) |
|---|---|---|---|---|---|---|---|---|---|---|---|---|---|
| 9 | Ex. 7 | 1.34 | | | FS-1 | 54.1 | 45.7 | | | | | | |
| | | | 80 | 100 | 1 | 39.6 | 38.8 | 19.5 | 1.6 | 7.9 | 10.9 | 78.2 | 80 |
| | | | 100 | 100 | 2 | 37.6 | 37.8 | 22.3 | 1.9 | 8.0 | 8.9 | 80.0 | 100 |
| | | | 120 | 100 | 3 | 34.5 | 36.2 | 26.9 | 2.4 | 8.3 | 7.9 | 80.1 | 121 |
| | | | 100 | 200 | 4 | 47.8 | 43.1 | 8.7 | 0.4 | 5.5 | 12.4 | 76.4 | 100 |
| | | | 100 | 300 | 5 | 49.6 | 44.2 | 5.7 | 0.2 | 4.2 | 12.8 | 72.8 | 100 |

TABLE 10
NONYLPHENOL

| Ex. | Catalyst | PhOH/C₄H₈ Molar Ratio | Control Temp. (°C.) | Feed Rate (cc/hr) | Sample | glc Temp C₉H₁₈ | PhOH | NP | lc DNP | DNP | o-NP | p-NP | Hot Spot (°C.) |
|---|---|---|---|---|---|---|---|---|---|---|---|---|---|
| 10 | Ex. 8 | 1.34 | | | FS-1 | 50.4 | 47.7 | | | | | | |
| | | | 80 | 100 | 1 | 40.9 | 42.2 | 15.6 | 0.7 | 4.5 | 7.0 | 84.8 | 80 |
| | | | 100 | 100 | 2 | 38.3 | 40.6 | 19.6 | 0.9 | 4.0 | 5.2 | 87.0 | 101 |
| | | | 120 | 100 | 3 | 37.0 | 43.8 | 18.2 | 0.2 | 4.0 | 4.7 | 87.1 | 120 |
| | | | 100 | 200 | 4 | 47.1 | 48.3 | 3.4 | | 3.2 | 6.7 | 83.6 | 100 |
| | | | 100 | 300 | 5 | 47.3 | 47.8 | 4.3 | | 3.0 | 6.7 | 80.7 | 100 |

<sup>a</sup>HF on Linde SK-500, 1/16" E
<sup>b</sup>100 cc capacity unit, run at 100 psi
<sup>b</sup>100 cc catalyst unit, run at 100 psi

TABLE 11
NONYLPHENOL

| Ex. | Catalyst | PhOH/C₄H₈ Molar Ratio | Control Temp. (°C.) | Feed Rate (cc/hr) | Sample | glc Temp C₉H₁₈ | PhOH | NP | lc DNP | DNP | o-NP | p-NP | Hot Spot (°C.) |
|---|---|---|---|---|---|---|---|---|---|---|---|---|---|
| 11 | C861β | 1.34 | | | FS-1 | 49.0 | 45.9 | 4.3 | 0.6 | | | | |
| | | | 80 | 100 | 1 | 33.2 | 38.5 | 27.1 | 0.4 | 1.1 | 7.5 | 85.7 | 80 |
| | | | 100 | 100 | 2 | 28.8 | 34.9 | 34.8 | 0.8 | 2.2 | 10.0 | 83.3 | 100 |
| | | | 120 | 100 | 3 | 18.1 | 27.8 | 51.6 | 0.9 | 3.8 | 12.0 | 81.7 | 120 |
| | | | 100 | 200 | 4 | 39.2 | 41.9 | 17.9 | 0.3 | 1.6 | 10.5 | 82.1 | 100 |
| | | | 100 | 300 | 5 | 43.8 | 46.1 | 9.3 | 0.1 | 1.2 | 11.1 | 80.9 | 100 |

What is claimed is:

1. A one-step method for synthesis of alkylphenols which comprises reacting phenol with the corresponding olefin under adiabatic conditions in the presence of a catalyst comprising a zeolite molecular sieve at a 7. The method of claim 1 wherein Y-zeolite has been dealuminated by ammonium exchanging followed by calcinating.

8. The method of claim 1 wherein the Y-zeolite has been dealuminated by chelating the alumina with ethylenediaminetetraacetic acid.

9. The method of claim 1 wherein the Y-zeolite has been dealuminated by treating the zeolite with a compound from the group consisting of hydrofluoric acid, silicon tetrafluoride and ammonium fluorosilicate.

10. The method of claim 1 wherein Y-zeolite has been dealuminated by steaming or acid leaching or the combined steaming and acid treatment.

11. The method of claim 1 wherein the maximum operating temperature is in the range of 80° to 140° C.

12. The method of claim 3 wherein the nonenes to phenol molar feed ratio is 1:5 to 5:1.

13. A one-step method for synthesis of nonylphenols which comprises reacting phenol with the corresponding nonene under adiabatic conditions in the presence of a catalyst comprising a dealuminated Y-zeolite wherein dealumination is accomplished by a method selected from:

Ammonium exchanging followed by calcinating;
Chelating the alumina with ethylenediaminetetraacetic acid;
Treating the Y-zeolite with a fluorine-containing compound; and
Treating the Y-zeolite with steam, acid or the combined steam/acid.

14. The method of claim 13 wherein the dealuminated Y-zeolite has a silica-to-alumina molar ratio in the range 5 to 100 and a unit cell size in the range 24.2 to 24.6Å.

15. The method of claim 13 wherein the dealuminized Y-zeolite has a silica-to-alumina ratio of 46, surface area of 775 m$^2$/g and a unit cell size of 24.26Å as 1/16" extrudates.

16. The method of claim 13 wherein the dealuminized Y-zeolite has a silica-to-alumina ratio of 6.5, a surface area of 800 m$^2$/g and a unit cell size of 24.56Å.

17. The method of claim 13 wherein the Y-zeolite is an ultrastable Y-zeolite in sodium form having a silica-to-alumina ratio of 5.3, a surface area of 750 m$^2$/g and unit cell size of 24.51Å.

18. The method of claim 13 wherein the dealuminized Y-zeolite has a silica-to-alumina ratio of 7.8 and a unit cell size of 24.53Å.

19. The method of claim 13 wherein the dealuminated Y-zeolite catalyst is in combination with a binder from the group consisting of alumina and silica/alumina.

20. The method of claim 19 wherein the dealuminated Y-zeolite is a rare earth exchanged Y-zeolite having a Si/Al ratio of 1.5→2 and wherein 10–20% of the catalyst is alumina binder.

21. The method of claim 4 wherein the Y-zeolite is modified with triflic acid.

22. The method of claim 1 wherein the zeolite is a $\beta$-zeolite.

23. The method of claim 21 wherein the Y-zeolite is a rare-earth exchanged Y-zeolite and the modified Y-zeolite has a fluoride content of 2.3% and an acidity of 0.33 meq/g.

24. The method of claim 22 wherein the $\beta$-zeolite has a silica-to-alumina ratio of 24, a surface area of about 600 m$^2$/g and is in 1/16" extruded form.

* * * * *